(12) United States Patent
Scanlan et al.

(10) Patent No.: US 12,311,178 B2
(45) Date of Patent: May 27, 2025

(54) NERVE REGENERATION SYSTEM AND METHOD

(71) Applicant: CHECKPOINT SURGICAL, INC., Cleveland, OH (US)

(72) Inventors: Kevin Scanlan, Cleveland, OH (US); Eric R. Walker, Berea, OH (US); Leonard M. Cosentino, Hudson, OH (US)

(73) Assignee: CHECKPOINT SURGICAL, INC., Cleveland, OH (US)

( * ) Notice: Subject to any disclaimer, the term of this patent is extended or adjusted under 35 U.S.C. 154(b) by 0 days.

(21) Appl. No.: 18/238,155

(22) Filed: Aug. 25, 2023

(65) Prior Publication Data

US 2023/0398357 A1 Dec. 14, 2023

Related U.S. Application Data

(63) Continuation of application No. 17/123,331, filed on Dec. 16, 2020, now Pat. No. 11,766,567, which is a
(Continued)

(51) Int. Cl.
*A61N 1/36* (2006.01)
*A61N 1/04* (2006.01)
*A61N 1/05* (2006.01)

(52) U.S. Cl.
CPC ....... *A61N 1/36103* (2013.01); *A61N 1/0464* (2013.01); *A61N 1/0551* (2013.01); *A61N 1/36017* (2013.01); *A61N 1/36167* (2013.01)

(58) Field of Classification Search
CPC .............. A61N 1/36103; A61N 1/0464; A61N 1/0551; A61N 1/36017; A61N 1/36167; A61N 1/3605
See application file for complete search history.

(56) References Cited

U.S. PATENT DOCUMENTS

| 4,423,732 A | 1/1984 | Tarjan |
| 6,292,697 B1 | 9/2001 | Roberts |

(Continued)

FOREIGN PATENT DOCUMENTS

| WO | 2013036630 A1 | 3/2013 |
| WO | 2013067018 A2 | 5/2013 |

(Continued)

OTHER PUBLICATIONS

Sakuma, M., Minev, I. R., Gribi, S., Singh, B., Woolf, C. J., & Lacour, S. P. (2015). Chronic electrical Nerve stimulation as a therapeutic intervention for peripheral nerve repair. Bioelectronic Medicine, 2(1), 43-48. https://doi.org/10.15424/bioelectronmed.2015.00005 (Year: 2015).*

(Continued)

*Primary Examiner* — Paula J Stice
(74) *Attorney, Agent, or Firm* — McDonald Hopkins LLC

(57) ABSTRACT

A stimulation device includes an adaptor component. The adaptor component couples a percutaneous lead to the stimulation device. The stimulation device may apply a stimulation signal to target tissue via the adaptor. A surgeon may place the stimulation device in a container and the adaptor component may be disposed outside of the container. Methods describe prolonged stimulation of target tissue via a stimulation device. The prolonged stimulation may be applied during and after a surgical procedure.

34 Claims, 8 Drawing Sheets

Related U.S. Application Data continuation of application No. 16/623,538, filed as application No. PCT/US2018/039017 on Jun. 22, 2018, now Pat. No. 11,872,401.

(60) Provisional application No. 62/523,300, filed on Jun. 22, 2017.

(56) References Cited

U.S. PATENT DOCUMENTS

| | | | |
|---|---|---|---|
| 7,305,268 | B2 | 12/2007 | Gliner et al. |
| 7,483,747 | B2 | 1/2009 | Gliner |
| 8,972,022 | B2 | 3/2015 | Hincapie |
| 9,381,356 | B2 | 7/2016 | Parker |
| 9,782,591 | B2 | 10/2017 | Kramer |
| 2002/0120309 | A1 | 8/2002 | Richmond |
| 2003/0088274 | A1 | 5/2003 | Gliner |
| 2005/0203602 | A1 | 9/2005 | Wallace |
| 2008/0300655 | A1 | 12/2008 | Cholette |
| 2009/0132003 | A1* | 5/2009 | Borgens ............ A61N 1/37205 607/50 |
| 2010/0152812 | A1 | 6/2010 | Flaherty |
| 2012/0296442 | A1* | 11/2012 | Hausman ........... A61B 18/1477 623/23.72 |
| 2013/0197615 | A1 | 8/2013 | Rundle |
| 2014/0214135 | A1 | 7/2014 | Ben-David |
| 2014/0275847 | A1* | 9/2014 | Perryman .......... A61N 1/36038 607/45 |
| 2016/0206876 | A1* | 7/2016 | Rajguru ................ A61N 2/02 |
| 2016/0339239 | A1 | 11/2016 | Yoo |
| 2017/0136244 | A1 | 5/2017 | Bonde |
| 2017/0165497 | A1 | 6/2017 | Lu |
| 2017/0281945 | A1 | 10/2017 | Gill |
| 2020/0101290 | A1 | 4/2020 | Rockley |
| 2021/0146121 | A1 | 5/2021 | Scanlan et al. |

FOREIGN PATENT DOCUMENTS

| | | |
|---|---|---|
| WO | 2016183689 A1 | 11/2016 |
| WO | 2018237278 A1 | 12/2018 |

OTHER PUBLICATIONS

Foecking EM, Fargo KN, Coughlin LM, Kim JT, Marzo SJ, Jones KJ. Single session of brief electrical stimulation immediately following crush injury enhances functional recovery of rat facial nerve. J Rehabil Res Dev. 2012;49(3):451-8. doi: 10.1682/jrrd.2011.03.0033. PMID: 22773203 (Year: 2012).*

Calvey, C., Zhou, W., Stakleff, K. S., Sendelbach-Sloan, P., Harkins, A. B., Lanzinger, W., & Willits, R. K. (2015). Short-Term electrical stimulation to promote nerve repair and functional recovery in a RAT model. The Journal of Hand Surgery, 40(2), 314-322. https://doi.org/10.1016/j.jhsa.2014.10.002 (Year: 2015).*

Patent Cooperation Treaty (PCT), International Search Report and Written Opinion for Application PCT/US2018/039017 filed Jun. 22, 2018, mailed Sep. 17, 2018; International Searching Authority, EP.

Alrashdan et al., "Thirty minutes of low intensity electrical stimulation promotes nerve regeneration after sciatic nerve crush inury in a rat model", Acta Neurol. Belg., 110, pp. 168-179, 2010.

Al-Majed et al., "Brief electrical stimulation promotes the speed of accuracy of motor axonal regeneration," The Journal of Neuroscience, 20(7): pp. 2602-2608, 2000.

Sakuma et al., "Chronic electrical nerve stimulation as a therapeutic intervention for peripheral nerve repair," Bioelectronic Medicine, 2, pp. 43-48, 2015.

Examination Report No. 1 in AU2018290344, mailed Mar. 29, 2023, 7 pages.

Examination Report No. 2 in AU2018290344, mailed Oct. 12, 2023, 6 pages.

* cited by examiner

NERVE REGENERATION SYSTEM AND METHOD

CROSS-REFERENCE TO RELATED APPLICATION(S)

This application is a continuation of U.S. Utility application Ser. No. 17/123,331 entitled "NERVE REGENERATION SYSTEM AND METHOD," filed on Dec. 16, 2020, now U.S. U.S. Pat. No. 11,766,567 which is a continuation of U.S. Utility application Ser. No. 16/623,538 entitled "NERVE REGENERATION SYSTEM AND METHOD," filed on Dec. 17, 2019, now U.S. U.S. Pat. No. 11,872,401 which is a 35 U.S.C. 371 national stage filing and claims priority to International Application No. PCT/US2018/039017 entitled "NERVE REGENERATION SYSTEM AND METHOD," filed on Jun. 22, 2018, which claims the benefit of U.S. Provisional Patent Application No. 62/523,300, entitled "NERVE REGENERATION SYSTEM AND METHOD," filed on Jun. 22, 2017, each of which are hereby incorporated by reference.

FIELD OF THE INVENTION

The invention relates generally to nerve regeneration, and more particularly to systems and methods for accelerating or enhancing regrowth of injured or potentially injured nerves undergoing treatment or surgical repair.

BACKGROUND OF THE INVENTION

Nerve injuries present clinicians with significant challenges in determining the proper course of treatment to restore impaired motor and or sensory function. Ultimately, the severity of the nerve injury and time post injury have the greatest influence on the treatment plan and potential for success. In many cases surgical intervention may be needed to increase the likelihood that control of muscle function or sensation can be regained. Surgical treatment of nerve injuries typically does not provide immediate restoration of function, as nerve fibers must grow from the point of intervention or repair to the target muscle. Nerve fibers grow at a rate of 1 mm/day, and thus recovery takes a significant amount of time.

Despite advancements in surgical technique and medical device technology, the rate of growth and organization of fiber growth direction remains a significant factor limiting functional outcomes.

It may be desirable to provide a method for delivering a period of electrical stimulation as soon as possible, prior to or following repair, preferably while still in the operating room, to improve functional outcome. Furthermore, it may be desirable to be able to initiate a period of stimulation in the operating room and continuing into a post-operative setting without interrupting stimulation. It may alternatively or additionally be desirable to initiate stimulation during surgery or after surgery. Moreover, stimulation may be initiated in an office or an operating room and may continue while the patient moves between rooms. Additionally, it may be desirable to deliver repeated periods of stimulation during recovery, without the need to replace electrode(s) before each application.

SUMMARY OF THE INVENTION

The following presents a summary of this disclosure to provide a basic understanding of some aspects. This summary is intended to neither identify key or critical elements nor define any limitations of embodiments or claims. Furthermore, this summary may provide a simplified overview of some aspects that may be described in greater detail in other portions of this disclosure.

A system for stimulating tissue is described herein. The stimulation system may include a stimulation device comprising a housing, control circuitry disposed within the housing, an operative element coupled with the housing and comprising at least one electrode, a percutaneous lead operatively attachable to the stimulation device, and a container operatively receiving the stimulation device, wherein the container comprises at least one connection port that operatively and electrically couples the stimulation device to the percutaneous lead.

A method for stimulating tissue is described herein. The method may include performing a subcutaneous operating with a handheld stimulation device, placing a percutaneous lead at a target tissue region, wherein the percutaneous lead is operatively attached to a stimulation device that may be handheld, closing an incision, and applying a stimulation signal to the target tissue region with the percutaneous lead and the stimulation device after the closing of the incision.

The following description and the drawings disclose various illustrative aspects. Some improvements and novel aspects may be expressly identified, while others may be apparent from the description and drawings.

BRIEF DESCRIPTION OF THE DRAWINGS

The accompanying drawings illustrate various systems, apparatuses, devices and methods, in which like reference characters refer to like parts throughout.

Figure 1:
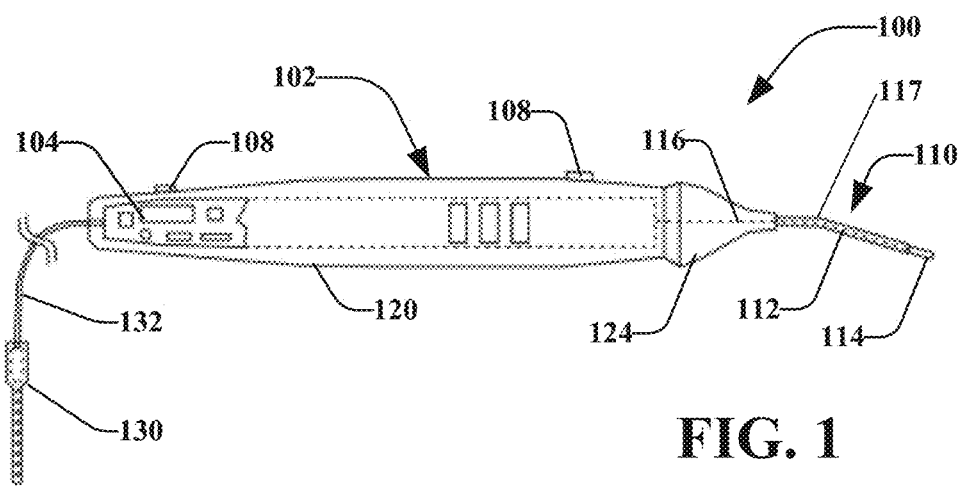
FIG. 1 illustrates a partial cross-sectional view of a stimulation device, in accordance with various disclosed aspects.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

Reference will now be made in detail to exemplary embodiments of the present invention, examples of which are illustrated in the accompanying drawings. It is to be understood that other embodiments may be utilized, and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggests otherwise.

It is noted that the various embodiments described herein may include other components and/or functionality. It is further noted that while various embodiments refer to a stimulator or stimulation device, various other systems may be utilized in view of embodiments described herein. For example, embodiments may be utilized in a variety of surgical procedures. As such, embodiments may refer to a particular surgical procedure for purposes of explanation. It is noted that aspects of embodiments, however, may be utilized for various other procedures.

This disclosure generally relates to systems and methods that may improve nerve regeneration or neuroregeneration of tissue via electrical stimulation to increase the speed or amount of nerve growth. The terms "nerve" or "nerve tissue" generally refer to any portion of a nerve including, but not limited to, axons, axon terminals, somas, dendrites, or the like, unless context suggest otherwise. Moreover, aspects disclosed herein may be applicable to nerve tissue throughout a body, whether peripheral nervous tissue or otherwise. Further, while embodiments may reference a surgeon performing a particular action(s), it is noted that other users, automated machines, or the like may perform such actions.

It is noted that described systems and methods may be utilized in combination with various systems and methods for safeguarding against nerve, muscle, and tendon injury during surgical procedures or confirming the identity and/or location of nerves, muscles, and tendons and evaluating their function or the function of muscles enervated by those nerves. The systems and methods are particularly well suited for assisting in nerve regeneration via a device that may also be utilized by a surgeon in identification of nerves and muscles in order to assure nerve and muscle integrity during medical procedures using medical devices such as stimulation monitors, cutting, drilling, and screwing devices, pilot augers, and fixation devices. Further, the systems and methods may be utilized in surgery so as to identify the nerve and/or to deliver stimulation for nerve regeneration. This stimulation may be delivered during surgery prior to repair or treatment of the nerve injury and/or following repair or treatment of the nerve injury and/or continue post-surgery. It is noted, however, that various disclosed aspects may be utilized independent of such systems and methods.

For example, a surgeon may utilize a handheld stimulation device to generate a stimulation signal at sufficiently high levels for the purposes of locating, stimulating, and evaluating nerve or muscle, or both nerve and muscle integrity in numerous medical procedures, including, but not limited to, evaluating proximity to a targeted tissue region, evaluating proximity to a nerve or to identify nerve tissue, evaluating nerve integrity (i.e., following a traumatic or repetitive motion injury) to determine if a repair may be needed, evaluating muscle contraction to determine whether or not the muscle is innervated and/or whether the muscle is intact and/or whether the muscle is severed, identifying specific nerve branches or fascicles for repair or transfer, and evaluating muscle and tendon length and function following a repair or tendon transfer prior to completing a surgical procedure. Before, after or during a procedure, a surgeon may place an electrode or lead on or near the nerve to be stimulated and/or proximal to the site of injury or repair. The electrode may be percutaneous or non-percutaneous (e.g., surface electrode). In an aspect, a percutaneous lead may be taped or otherwise held in place on a patient's skin. This may allow for easy removal after the prolonged stimulation. One exemplary embodiment of such comprises a patch that may be adhered to the skin of a patient. The patch may generally circumscribe the insertion point of the percutaneous lead and may allow a portion of the lead to extend therethrough. In this embodiment, a connector may be utilized to operatively couple of the percutaneous lead with the stimulation device. Alternatively, the lead may be operatively coupled with the patch and the patch may include an adapter that operatively couples with the stimulation device. The patch may include an electrical path between the percutaneous lead and the adapter such that electrical stimulation may pass from the stimulation device through the patch and to the percutaneous lead. The lead may be coupled to a stimulation device that was used during surgery, or another stimulation device, via a wire or other connector. The stimulation device may be placed in a sealed housing to prevent contamination when leaving the operating room into a post-operative setting or to maintain a fixed position. The housing may comprise a port that may allow the lead to be coupled with the stimulation device, and another port to connect a percutaneous or surface electrode, such as a patch, as a return current path. The stimulation device may generate a signal to stimulate the nerve tissue.

In an aspect, the stimulation device may generate the signal to stimulate the nerve tissue following a procedure or prior to surgical completion. Placement of a percutaneous lead may allow a surgeon to place the lead and stimulate the nerve with a stimulation device during or after the surgery, without requiring the surgeon to hold the stimulation device in place. In an aspect, the stimulation may take place generally after a procedure for a predetermined period (e.g., i minutes, where i is a number). In at least one embodiment, the stimulation may take place for about an hour or less after a procedure has been completed. Stimulation immediately after a procedure (e.g., nerve transfer or nerve release) may increase the speed, quality, or amount of nerve regeneration. An aspect enables the onset of stimulation to begin in the operating room, prior to procedure completion, and continuing into a post-operative setting, without disrupting stimulation. Reduction of the delay from the completion of surgical intervention to start of stimulation, may provide further clinical benefit.

In one example, electrical stimulation may be applied to determine a baseline level of nerve excitability at the start of a surgery, i.e., a threshold test. During or near completion of the surgery a second test of nerve excitability may be conducted. This second test may be compared against the first. If the second test results in lower nerve excitability, prolonged stimulation may be applied after the surgery to help with nerve regeneration. This entire series of tests may be done with a single electrode and stimulation device or may be accomplished with two or more electrodes or stimulation devices. Further still, the initial threshold test may be done with a different stimulation and the same lead or a different stimulation device and lead or with the same stimulation device and the same lead. The application of the second test may determine if the nerve regeneration stimulation is necessary or desirable for the patient, i.e., to treat any potential nerve injury or trauma as suggested by the reduction in nerve excitability between the first and second test. The threshold test may comprise electrical stimulation to a nerve or nerves within a target tissue region to determine or measure the excitability of the nerve or nerves. In such situations, it may only be necessary to test nerve excitability to determine if the nerve regeneration therapy is needed prior to applying such nerve regeneration therapy. Threshold testing may be done at any time during the surgery, such as when a retractor is removed, a limb of a patient has a force applied to it or the like.

In another example, stimulation of a nerve may be applied during surgery prior to treatment or repair of nerve damage, suspected nerve damage, a risk of future nerve damage, or the like. A percutaneous lead may be placed at or near a nerve (e.g., within a range of the signal) to allow a stimulation device to generate and apply a signal to the nerve tissue. The stimulation may take place for a predetermined period of time and may be conducted at any time during surgery. For example, stimulation may occur immediately at the start of surgery and may be conducted for an hour or less. It is noted that the stimulation may be apply at different strengths, frequencies, patterns, or the like. Stimulation at time of a surgical operation may increase the speed, quality, or amount of nerve regeneration or nerve function recovery. The percutaneous lead may be anchored, held, or otherwise left in place after stimulation, during, and/or after a surgical operation.

As described herein, the parameters of the stimulation signal of the prolonged stimulation may be preprogrammed or may be set by a surgeon. In at least one embodiment, the pulse width may be held constant (e.g., not adjusted) during the stimulation. In an aspect the stimulation signal may be applied at generally between 15-30 Hz, or about 16 Hz. The amplitude of the stimulation may be held constant or be adjusted by the surgeon. In general the stimulation amplitude will generally be between 0.1-20 mA, typically between 1.0-2.0 mA. Moreover, the stimulation signal may be applied for a prolonged period (e.g., an hour). It is noted that the prolonged stimulation signal may be applied in a single dose or multiple doses, or for durations up to or more than 8 hours. For example, multiple doses may be applied through the same percutaneous lead, which may be kept in place between doses or may be removed between the doses. In such examples, one lead may be utilized and a different stimulation device utilized depending upon the location of the patient during stimulation, i.e., surgical location or post-operative location. In the alternative, one lead may be utilized and a single stimulation device utilized regardless of the location of the patient during stimulation. In yet another alternative, a different lead and different stimulation device may be utilized depending upon the location of the patient during stimulation. In such dosing examples, the electrical stimulation may be applied for a period of time, such as k minutes, where k is a number (e.g., 1, 2, 5, 10, 15, 60, etc.). In an example, the period may be between about 10 minutes and an hour or more.

For example, stimulation systems described herein may intraoperatively deliver, for a period of time, an electrical stimulation to repaired peripheral nerves. An attachment (e.g., a percutaneous electrode lead attachment such as those described in U.S. Patent Application US2014/0073985A, which is incorporated by reference herein) may be coupled with a stimulation device after a surgical procedure. It is noted that the stimulation device may be a stimulation device that was used during the procedure. For instance, a surgeon may utilize a handheld stimulation device to access nerve function during a surgical operation. The surgeon may place one or more implantable leads at a position where the lead may stimulate nerves that may have damage, potential for damage, or may require recovery after completion of the surgical operation. It is important to note that the present disclosure contemplates providing the electrical stimulation to be preventative, i.e., to mitigate the impact of a nerve injury, risk of nerve injury, or suspect nerve injury. The surgeon may, for instance, place the handheld stimulation device into a sterilized container and may electrically attach the one or more implantable leads to the handheld stimulation device via ports of the container. As such, the patient's nerve may be stimulated post operatively via the same stimulation device utilized for the surgical operation. Once post-operative stimulation is completed (e.g., after 1 hour of stimulation), the stimulation device may be discarded or otherwise removed.

The stimulation device may be disposable or reusable. Described systems may allow a stimulation electrode to be placed intraoperatively, in close proximity to the nerve to be stimulated; allowing the lead to pass out of the tissue and attach to the stimulation device.

The stimulation device may provide a prolonged stimulation after an incision is closed. At a desired stopping time, the lead may be removed post operatively, and the prolonged course of stimulation may be discontinued. In an aspect, this may eliminate the need for extended operating time, and may free up a surgeon or staff from holding the stimulator on the nerve for prolonged stimulation. The lead may also be left in for a period of time, to enable repeated doses of stimulation across multiple days or weeks without need for placement of another lead.

The surgeon may place the stimulation device in a container. The container may comprise a bag, box, or other container. The container may seal the stimulation device within the container to prevent or reduce the chance of contamination, provide stability, or the like. In at least one embodiment, the container may comprise one or more ports that may allow the stimulation device to be coupled with a wire or lead. The return current electrode may be attached to a side of the container that is in contact with a patient, or may be an external electrode that connects to a second port on the container. As described herein, the container may comprise a suitable material such as a plastic, vinyl, metal, or other material.

It is noted that the disclosed systems and methods are applicable for use in a wide variety of medical procedures involving peripheral nerves. By way of non-limiting example, the various aspects of the invention have application in treatment of nerve transection injuries, nerve crush injuries, suspected nerve injuries, risk of nerve injuries or function reduction, or nerve transfer procedures, including, without limitation nerve decompression procedures (such as carpal tunnel or cubital tunnel syndrome), neurolysis, nerve transfer, nerve repair (such as direct repair, autograft, allograft, or conduit), and iatrogenic injury (thermal, stretch, compression, or transection).

In at least one embodiment, an electrical stimulation system may comprise a stimulation device and an adaptor. The stimulation device may comprise housing, control circuitry operatively generating a stimulation signal, wherein the control circuitry is disposed within the housing, and an operative element coupled with the housing and comprising at least one electrode. The adaptor may be selectively attached to the operative element, and may comprise a percutaneous lead electrically coupled to the stimulation device through the at least one electrode, the percutaneous lead insertable into a patient during a subcutaneous surgery and after the subcutaneous surgery and wherein the stimulation device is capable of applying electrical stimulation during the subcutaneous surgery and after the subcutaneous surgery. The percutaneous lead may comprise a twisted wire.

The control circuitry may apply the electrical stimulation after the subcutaneous surgery for nerve regeneration therapy. Nerve regeneration therapy may comprise stimulation to a nerve to alter recovery (e.g., improve, enhance, accelerate, etc.) of the nerve so stimulated. In another aspect, the control circuitry may apply the electrical stimulation for a period between 10 minutes and one hour. The electrical stimulation system may further comprise a container operatively receiving the stimulation device, wherein the container comprises at least one connection port that operatively and electrically couples the stimulation device to the percutaneous lead. In at least one embodiment, the electrical stimulation system may further comprise a splitter device, operatively coupled to the stimulation device, electrical stimulation system, and at least one other lead, wherein the splitter device receives the stimulation signal and generates generally uniform output signals to the lead and the at least one other lead. The splitter device may be disposed within the container. The container may comprise an attachment device that operatively attaches the container to an object. The container may additionally or alternatively comprise one or more fasteners to selectively secure the control circuitry within the container. It is noted that the at least one connection port may comprise a return port that operatively receives a return electrode of the stimulation device from within the container. The return port may operatively and electrically couple the return electrode to a return lead.

In another aspect, embodiments include a method for stimulating tissue may comprise In another aspect, embodiments include a method for stimulating tissue may comprise performing a subcutaneous surgery with a stimulation device, placing a lead within range of a target tissue region, wherein the lead is operatively attachable to the stimulation device, and applying a stimulation signal to the target tissue region with the lead and the stimulation device before or after the subcutaneous surgery. Placing the lead may comprise placing the lead percutaneously. The stimulation device may be a handheld stimulation device. The method may include placing the stimulation device within a container after performing the subcutaneous surgery and for nerve regeneration therapy. It is noted that the method may include attaching the lead to an external end of a port of the container and attaching the stimulation device to an internal end of the port. According to at least one example, the stimulation device is placed within the container while in an operating room. Moreover, stimulating the target tissue region with the lead and the stimulation device may be done prior to performing certain portions of the subcutaneous surgery or during the subcutaneous surgery to determine a threshold for excitability of a nerve within the target tissue region, for the purpose of determining if application of prolonged stimulation for nerve regeneration therapy is appropriate. In an aspect, the determined threshold for excitability may be utilized to determine if application of stimulation for nerve regeneration therapy is appropriate.

A method for stimulating tissue may comprise placing a lead within range of a target tissue region and applying a stimulation signal with a stimulation device; and performing a subcutaneous surgery with the handheld stimulation device before or after applying the stimulation signal. The method may further comprise storing the stimulation device within a container prior to moving out of an operative setting in order to maintain sterility after and stability while moving a patient to another location. In at least some embodiments, the method may comprise stimulating the target tissue after performance of the subcutaneous surgery.

Figure 2:
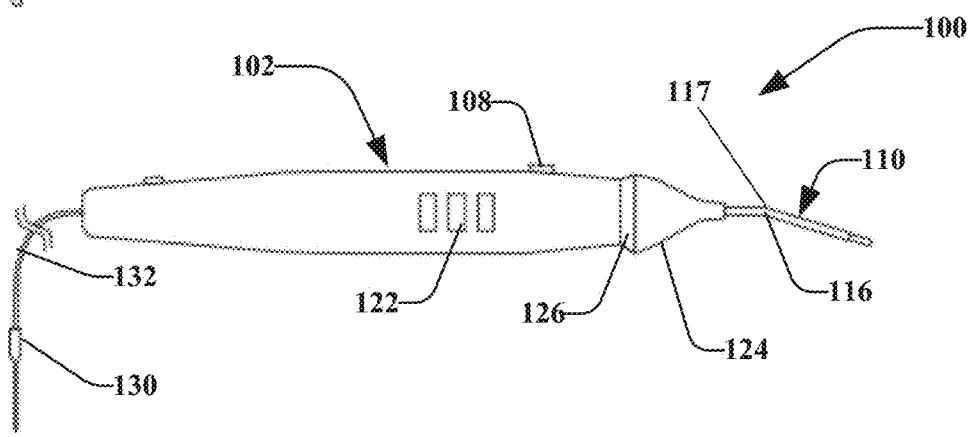
FIG. 2 illustrates a side view of the stimulation device of FIG. 1, in accordance with various disclosed aspects.

Turning now to FIGS. 1 and 2, there is a stimulation system 100 that may comprise a stimulation device 102 configured for locating, monitoring, and stimulating tissue and other structures throughout the body. The stimulation system 100 may be utilized for locating and identifying tissue and safeguarding against tissue and/or bone injury during surgical procedures. In another aspect, the stimulation device 102 may be utilized for percutaneously stimulating a nerve after a surgery for a desired amount of time. In an aspect, the stimulation may be post-operative stimulation after a surgical procedure.

The stimulation device 102 may include or be coupled with one or more attachments or operative elements including, for example, a probe 110 (e.g., which may be blunt, needle-like, etc.), a cutting device, a drilling or screwing device, a pilot auger, and a fixation device. It is noted that attachments may be removable, attachable, or permanently affixed to the stimulation device 102. It is noted that while embodiments may describe use of a particular attachment (e.g., probe 110) for simplicity of explanation, the various embodiments may utilize other types of attachments.

In an exemplary embodiment, stimulation device 102 comprises control circuitry 104, disposed in a housing 120, that may apply a stimulation signal to a desired tissue region.

The control circuitry 104 may be coupled to a power source, such as a battery, power mains, or the like. The control circuitry 104 may generate the stimulation signal with desired parameters, as described herein. In an aspect, a user may adjust parameters and/or control the control circuitry 104 to generate the stimulation signal via one or more user interfaces 108, which may comprise at least one of a switch, button, slide, touch screen, or the like.

For instance, a user may grasp the stimulation device 102 via the housing 120. The housing 120 may include gripping portion 122. The gripping portion 122 may comprise indents, protrusions, elastomeric material, roughened material or other features that may aid in the user grasping the stimulation device. The gripping portion 122 of the housing 120 may include an over molded portion that may comprise all or part of the length of the housing 120. In an aspect, the over molded portion may comprise a thermoplastic elastomer material. It is noted that gripping portion 122 may be removable, attached to, or integrally formed with the housing 120.

In an example, a user may position the probe 110 so that an uninsulated or stimulating portion or electrode 114 is at a desired location. The user may interact with one or more of the user interfaces 108 to control delivery of stimulation signal, generated by the control circuitry 104, to the desired tissue region. The gripping portion 122 may aid in a user's efforts to hold the stimulation device 102. In an aspect, the control circuitry 104 communicates the stimulation signal to the stimulation probe 110 via a lead 112 that may travel through an insulated portion 117 of the probe to the uninsulated portion 114.

It is noted that the probe 110 may comprise one or more flexible materials (e.g., metal, plastic, etc.) so that a user may bend or otherwise manipulate the probe 110. In another aspect, the stimulation device 102 may comprise a nose cone 124 that may be flexible or rigid. An operative element (e.g., probe 110) may extend from the proximal end of the nose cone 124. The user may apply pressure to the nose cone 124 so that it moves or otherwise manipulates the probe 110. This may allow a surgeon or other user to position the uninsulated portion 114 at a desired position of a targeted tissue region. For example, the uninsulated portion 114 of the probe 110 is positioned in electrical conductive contact with at least one of muscle, nerve, or other tissue.

A flexible nose cone 124 may allow the surgeon to use either a finger or a thumb positioned on the nose cone 124 to make fine adjustments to the position of stim probe 110 at the targeted tissue region. The surgeon may grasp the housing 120 with the fingers and palm of the hand, and position the thumb on the nose cone 124, and with pressure applied with the thumb, cause the probe 110 to move while maintaining a steady position of the housing 120. This flexible nose cone 110 may allow for increased control of the position of the probe 110 with the movement of the surgeon's thumb (or finger, depending on how the stimulating probe is held). In another aspect, the nose cone 124 may comprise gripping components, such as ribs, indents, roughened surfaces, or the like.

It is noted that the nose cone 124 may comprise a single piece or it may comprise one or more pieces attached together. For example, nose cone 124 may comprise an inner portion that may include thermoplastic material having flexibility (e.g., LUSTRAN® ABS 348, or similar material), and an outer portion that may comprise a softer over molded portion and may be made of a thermoplastic elastomer material having flexibility (e.g., VERSAFLEX™ OM 3060-1 from GLS Corp). It is noted, however, that nose cone 124 may be generally rigid in at least some embodiments.

While described as a "cone" nose cone 124 may comprise a generally tapered shape. It is noted, however, that nose cone 124 may comprise other or different shapes (e.g., rounded, squared, prism, conical, etc.). Moreover, in embodiments, stimulation device 102 may not comprise a nose cone 124, such that probe 110 extends directly from housing 120.

As described herein, a simulation signal may flow from the stimulation device 102 through the lead 112 to the probe 110, which may act as an electrode. The stimulation system 100 may include one or more other electrodes, such as a return electrode, as described herein. For instance, in monopolar operation, a return electrode (or indifferent electrode) provides a return path for electrical signals passing through the tissue, and returning to the stimulation device 102. It is noted that stimulation system 100 may operate in a monopolar, bipolar or other configurations, as described here as well as elsewhere in this disclosure.

In various embodiments, the control circuitry 104 may generate the stimulation signal to operatively generate a physical motor response of a tissue (e.g., muscle, innervated muscle, nerve, etc.). The physical motor response may indicate whether the stimulation signal was delivered and/or whether a sufficient stimulation signal was delivered. For example, the motor response may include a physical motor response (e.g., twitching or contraction).

In another aspect, the stimulation device 102 may generate one or more visual or audio signals (e.g., via a speaker (not shown)), which indicate to the surgeon the status or diagnostic information. For instance, stimulation device 102 may comprise an indicator light 126. The indicator light may comprise one or more light sources, such as a light emitting diode (LED). In an aspect, the indicator light 126 may comprise a translucent (e.g., semi-translucent, fully translucent, etc.) surface that operatively shines or disperses light from an internal light source (not shown). In an aspect, the light source may generate light in one or more colors (e.g., green, yellow, blue, red, etc.), patterns (e.g., blink rate, pattern of colors, etc.), or the like. According to embodiments, the status or diagnostic information may indicate whether the stimulation signal was delivered and/or whether a sufficient stimulation signal was delivered. For example, the status or diagnostic information may indicate that an electric signal was returned from tissue, which may indicate sufficient proximity, contact, or delivery of a stimulation signal via an operative element (e.g., probe 110). In another aspect, the indicator light 126 may indicate that the stimulation device 102 is on/off, producing or not producing a stimulation signal, or the like.

In an example, the indicator light 126 allows the surgeon to confirm delivery of stimulus current to tissue. Through the use of different tones, colors, different flash rates, etc., the indicator 126 allows the surgeon to confirm that the uninsulated tip 114 is in place, the instrument is turned ON, and that stimulus current is flowing with sufficient delivery to tissue. Thus, the surgeon has a much greater confidence that the desired stimulation amplitude is being delivered to the nerve, as in the case of a nerve transfer of nerve graft, a muscle contraction will not be observed since the nerve is no longer in continuity. These indicators can be checked periodically to ensure stimulation is being delivered for the desired duration (e.g. between about 1 minutes and one hour).

As another example, in use the indicator 126 may be configured to illuminate continuously in one color when the stimulation device 102 is turned on but not in contact with tissue. After contact with tissue is made, the indicator 126 may flash (i.e., blink) to indicate that stimulation is being delivered. If the stimulation has been requested, i.e., the stimulation probe has been turned on, but there is no stimulation being delivered because of a lack of continuity between the probe 110 and the return electrode 130, or an inadequate connection of the probe 110 or the return electrode 130 to the patient tissue, the indicator 126 may illuminate in a different color, and may illuminate continuously or may flash.

As described herein, the indicator 126 may comprise a ring that provides a visual indication around at least a portion, and desirably all of the circumference of the stimulation device 102 generally near the nose cone 124. A ring indicator may be an element of the gripping portion 122, or it may be an element of the flexible nose cone 124, or the ring indicator may be positioned between the gripping portion 122 and the nose cone 124. The ring may also include a reflective element to improve and focus the illumination effect of the light emitting source, e.g., one or more LEDs. The ring and the reflective element may be a single component, or more than one component. Audio feedback also makes possible the feature of assisting the surgeon with monitoring nerve integrity during surgery.

While stimulation device 102 is described as generating an indication, it is noted that various other components of the stimulation system 100 may generate all or part of the indication. For instance, the stimulation device 102 (or a separate device) may monitor delivery of the stimulation signal. The stimulation device 102 may transmit status and diagnostic information (e.g. delivered current, stimulation duration, contraction presence, or the like) to a separate device (e.g., laptop, wearable electronic device, cellular phone, tablet, computer, speakers, light source, or the like). In an aspect, the stimulation device 102 may include a communication component that may be wired or wireless. For example, the stimulation device 102 may include a wireless transmitter/receiver configured to communicate via one or more communication protocols (e.g., Wi-Fi, BLUETOOTH, NFC, etc.).

In embodiments, stimulation device 120 may comprise a hand-held stimulation device. Housing 120 may be generally tubular, hexagonal, or other elongated shape. According to an aspect, the housing 120 may be ergonomic and sterile for use in operative procedures. For instance, the stimulation device 120 may be packaged in a sealed container that may allow a surgeon to open and use the stimulation device 120 without the need for sterilization. It is noted, however, that parts of the stimulation system 100 may be sterilized, such as probe 110. In another aspect, the stimulation device 120 may comprise a single use instrument for use during surgical procedures to identify nerves and muscles, muscle attachments, contract muscles to assess the quality of surgical interventions or the need for surgical interventions, evaluate the function of nerves already identified through visual means, or provide prolonged stimulation of a nerve.

The stimulation device 102 may be sized small enough to be held and used by one hand during surgical procedures, and may be ergonomically designed for use in either the left or right hand. In an embodiment, the stimulation device 120 may have a width of about 20 millimeters to about 30 millimeters, and desirably about 25 millimeters. The length of the stimulation device 120 (not including an operative element) may be about 18 centimeters to about 22 centimeters, and desirably about 20 centimeters. An operative element (e.g., probe 110) may also include an angle or bend 116 to facilitate assess to deep as well as superficial structures without the need for a large incision. As illustrated, the bend 116 may be generally downward, relative the directions shown in FIGS. 1 and 2. In an aspect, this may allow a surgeon to maintain a line of sight with target tissue and/or the uninsulated portion 114.

In one or more embodiments, as described here as well as elsewhere in this disclosure, an operative element may be mono-polar or bi-polar. For instance, probe 110 may be mono-polar. A return electrode 130 may be coupled to control circuit 104 via an insulated wire 132. The return electrode 130 may comprise any of a variety of electrode types (e.g., paddle, needle, wire, or surface electrode). In another aspect, the stimulation device 102 may be bipolar and may comprise a return electrode in the probe 110 or other operative element.

User interfaces 108 may allow a user to turn ON/OFF the stimulation device 102 (or set to standby), and may allow a user to control the stimulation signal amplitude selection within a predefined range (e.g., 0.1 0.5, 2.0, and/or 20 mA). In configurations, user interface 108 may be a four or five position switch. It is noted that the user interface 108 may allow for selection and change of frequencies within a range. Before the first use of the stimulation device 102, the user interface 108 is in the OFF position and keeps the stimulation probe off. After the user interface 108 has been turned ON (e.g., by moving the switch 155 to an amplitude selection), the OFF position now corresponds to a standby condition, where no stimulation would be delivered. In one embodiment, once the stimulation device has been turned on, it cannot be turned off, it can only be returned to the standby condition and will remain operational for a predetermined time, e.g., at least about seven hours. This may allow the stimulation device 102 to be only a single use device, so it cannot be turned OFF and then used again at a later date. It is noted, however, that some embodiments may allow the user to turn off the stimulation device 102 after it has been turned on. In one example, the user interfaces 108 may allow for selection of "prolonged stimulation." Once prolonged stimulation has been selected, the stimulation device 102 may disable user control of certain stimulation parameters, may allow the stimulation device 102 to be turned off, or may turn off after a certain time in the prolonged stimulation mode (e.g. 1 hour).

The user interfaces 108 may allow for adjustment of a stimulation signal pulse width from a predefined range (e.g., about zero to about 200 microseconds). In one embodiment, the user interfaces 108 may be a potentiometer to allow a slide control to increase or decrease the stimulation signal pulse width within the predefined range. The stimulation pulse may have a non-adjustable frequency in the range of about 10 Hz to about 30 Hz, and desirably about 16 Hz. In some embodiments, the stimulation pulse may comprise an adjustable frequency.

As a representative example, the stimulation pulse may have a biphasic waveform with controlled current during the cathodic (leading) phase, and net DC current less than 10 microamps, switch adjustable from about 0.1 milliamps to about 20 milliamps, and pulse durations adjustable from about zero microseconds up to about 1 millisecond.

The operative element (e.g., probe 110) exits or attaches to the housing 120 at the nose cone 124 to deliver stimulus current to the excitable tissue. The probe 110 comprises a length and a diameter of a conductive material, and is desirably fully insulated with the exception of the uninsulated portion 114, e.g. about 1.0 millimeters to about 10 millimeters, and desirably about 4 millimeters to about 6 millimeters, which is non-insulated and serves as the stimulating to allow the surgeon to deliver the stimulus The size of the uninsulated portion 114, (the active electrode) of the probe 110 ensures a high current density that will stimulate nearby excitable tissue. The insulation portion 112 may comprise a medical grade heat shrink.

The conductive material of the probe 110 comprises a diameter having a range between about 0.5 millimeters to about 1.5 millimeters, and may be desirably about 1.0 millimeters. The length of the operative element 110 may be about 50 millimeters to about 60 millimeters, although it is to be appreciated that the length may vary depending on the particular application. As shown, the probe 110 may include one or more bends 116 to facilitate accurate placement of the uninsulated portion 114. In one embodiment, the conductive material of probe 110 is made of a stainless steel, solid wire, although other conductive materials may be used. Further, the probe 110 may include an anchor 116. The anchor 116 may be of any appropriate configuration. By way of a non-limiting example, the anchor 116 may comprise a bend in the probe 110 such that upon insertion of the probe 110 into tissue of a patient, or more specifically, the anchor 116 being inserted into tissue of the patient, the anchor 116 prevents an undesired withdrawal of the anchor 116 and/or probe 110.

As previously described, in monopolar operation, a return electrode 131 (or indifferent electrode), for example, provides an electrical path from the body to the stimulation device 102. The return electrode 130 may be placed on the surface of intact skin (e.g., surface electrodes as used for electrocardiogic or electromyographic monitoring during surgical procedures) or it might be needle-like and be placed in the surgical field or penetrate through intact skin or an incision.

The configuration of the stimulating medical devices that form a part of the system can vary in form and function. Various representative embodiments of illustrative medical devices will be described.

Figure 3:
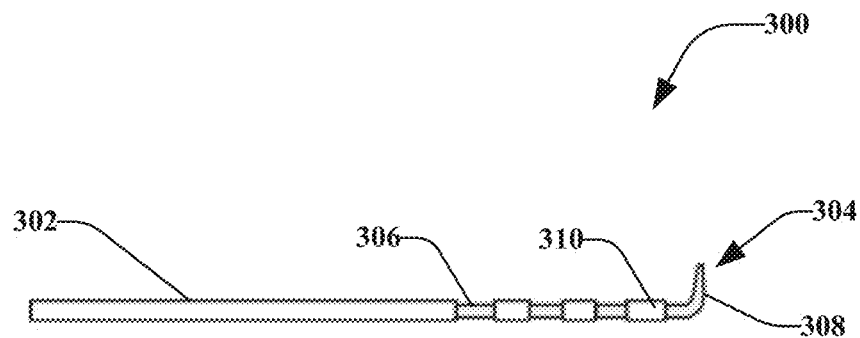
FIG. 3 illustrates a percutaneous electrode, in accordance with various disclosed aspects.
Figure 4A:
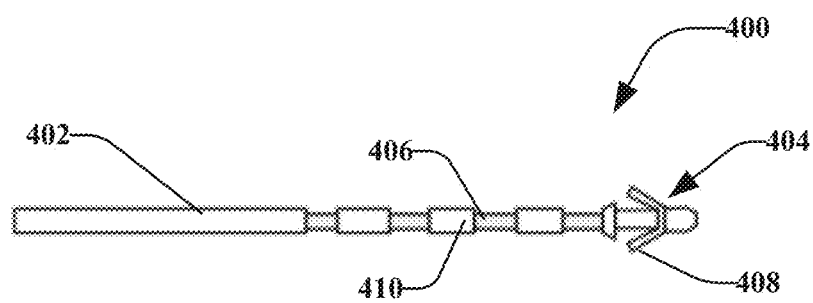
FIG. 4A illustrates another percutaneous electrode, in accordance with various disclosed aspects.

Referring now to FIGS. 3-4A, there are percutaneous electrodes 300 and 400 in accordance with various disclosed aspects. Percutaneous electrodes 300 and 400 may generally include an insulated body 302/402, an anchor 304/404, and one or more uninsulated portions 306/406. It is noted that percutaneous electrode 300 may comprise similar aspects as percutaneous electrode 400, unless context suggest otherwise or specific reference is made to a difference between the two. As such, while examples may refer to one of the percutaneous electrodes 300 and 400 for simplicity of explanation, the other may be utilized. Moreover, various other percutaneous electrodes may be utilized by embodiments disclosed herein.

In an example, percutaneous electrode 300 may be placed at or near a target tissue region and may be coupled with a percutaneous lead or wire, as described herein. It is noted that percutaneous electrode 300 may be positioned while an incision is open and may be left in place while the incision is closed. In at least one other embodiment, percutaneous electrode 300 may be positioned when an incision is closed or by deploying the percutaneous electrode 300.

In embodiments, percutaneous electrode 300 may comprise strands of stainless steel wire insulated with a biocompatible polymer. Each wire strand may have a diameter of approximately 34 μm and the insulated multi-strand lead wire may have a diameter of approximately 250 μm it should be understood, however, that these dimensions are merely exemplary and the present teachings are not limited to such. Any appropriate sized, shaped and configured electrode and percutaneous lead may be used. The insulated wire may be formed into a spiral or helix as has been found to accommodate high dynamic stress upon muscle flexion and extension, while simultaneously retaining low susceptibility to fatigue. The outer diameter of the percutaneous electrode 300 may be approximately 580 μm and it may be encased or filled with silicone or the like. In at least some embodiments, percutaneous electrode 300 may be made out of a different material (e.g., another metal, conducting polymer), may be insulated with another material, or may not be insulated. Further, the lead may be cylindrical or paddle-like.

Unlike surface electrodes that are applied to the surface of the patient's skin using an adhesive, percutaneous electrode 300 may be surgically implanted or otherwise inserted into select tissue. The terminal end or anchor 304 may comprise one or more tines 308 (e.g., tines 408 of percutaneous electrode 400). The anchor 304 may be insulated or uninsulated. In at least some embodiments, the anchor 304 may be inserted directly into tissue and may deliver stimulation signals to the tissue. In another aspect, the anchor 304 may generally hold the percutaneous electrode 300 in place. For instance, the one or more tines 308 may comprise a bend, curve, barb, etc., that prevents the percutaneous electrode 300 from substantially moving or unintentionally coming loose. As shown in FIGS. 3 and 4, disclosed embodiments may include different types of anchors 304/404. For instance, an anchor may include j tines, where j is a number. In an exemplary embodiment, a patch assembly may be utilized in conjunction with the percutaneous electrode 300. The patch assembly may comprise several layers, including an adhesive layer, an electrode layer, a reinforcement layer and a cover layer. In one embodiment, the patch assembly may include a power source for the stimulation device. Further, the patch assembly may act as a surface electrode. In one embodiment, the patch assembly may include engagement member or members that electrically couple the stimulation device to the percutaneous electrode 300 to provide stimulation for nerve regeneration. The engagement member may comprise a snap, a magnetic male and female member capable of operable engagement, a bayonet engagement device, or any know engagement mechanisms capable of electrically coupling the stimulation device with the percutaneous electrode 300. The present disclosure contemplates any such configuration of the patch assembly.

In another aspect, an anchor may include threaded members (e.g., screws) or the like. Further still, the percutaneous electrode 300 may not include any tines or anchors. In these embodiments, the percutaneous electrode 300 may be placed near or around, i.e., generally circumscribing all of or a portion of the applicable nerve. Further, the percutaneous electrode 300 may be placed over, i.e., on top of or at the bottom of, the applicable nerve, or near, i.e., in an operative distance from the applicable nerve in any manner. The present teachings are not limited to a specific configuration. Embodiments may include a nerve cuff, a coiled lead, a straight lead, lead with a hook, lead with a tine or tines, or the like.

According to embodiments, percutaneous electrode 300 may comprise flexible materials that allow some or all of the percutaneous electrode 300 to bend or deform. In an example, the insulated portion 302 may be a lead that is generally flexible to allow removal, positioning, or other manipulation of the percutaneous electrode 300.

In embodiments, sections of the uninsulated portion 306 may be separated by insulated portions 310 (e.g., insulation portions 410 in FIG. 4A). It is noted that different sections of the uninsulated portions 306 may be electrically isolated from each other to allow for bipolar stimulation. In another aspect, the insulated portions 310 may allow for increased strength, positioning, or the like of the percutaneous electrode 300. The uninsulated portion 306 may operatively deliver a stimulation current. It is noted that the uninsulated portion 306 may be disposed anywhere along the percutaneous electrode 300. For instance, the uninsulated portion 306 may be disposed at one or more tines 308, at anchor 304, or the like.

Figure 4B:
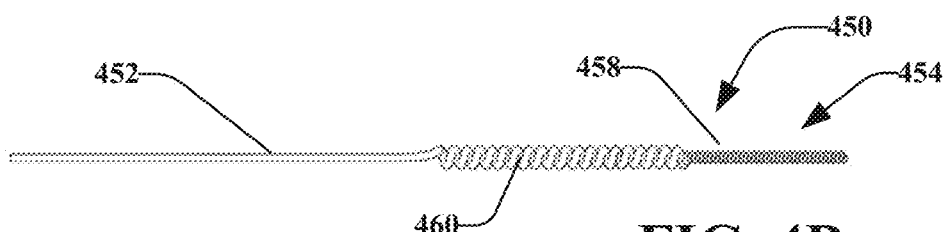
FIG. 4B illustrates another percutaneous electrode, in accordance with various disclosed aspects.

FIG. 4B illustrates another percutaneous electrode 450 comprising an insulated body 452 and an anchor 454. The anchor 454 may comprise a twisted or braided wire. The anchor 454 may be electrically conducting and not insulated such that it may apply a stimulation signal to tissue. In an aspect, the anchor 454 may comprise a helical portion 458. In another aspect, body 452 may include twisted, braided or helical portion 460. The helical portion 458 and helical portion 460 may anchor the percutaneous electrode 450 in places. In an aspect, the percutaneous electrode 450 may allow for extended use or implantation. For example, tissue may heal around the helical portion 458 or helical portion 460. The shape of these portions allows tissue to grasp and grow in between turns or bends of the helical portion 458 and helical portion 460. The tissue growth will anchor the percutaneous electrode 450 and may prevent or reduce chances of developing infections as the tissue heals around the percutaneous electrode 450. This may allow the electrode 450 to remain in place for an extended period of time or for a short period of time. Further, the helical portion 460 may comprise a fine-coiled wire with a insulative material surrounding such.

Figure 5:
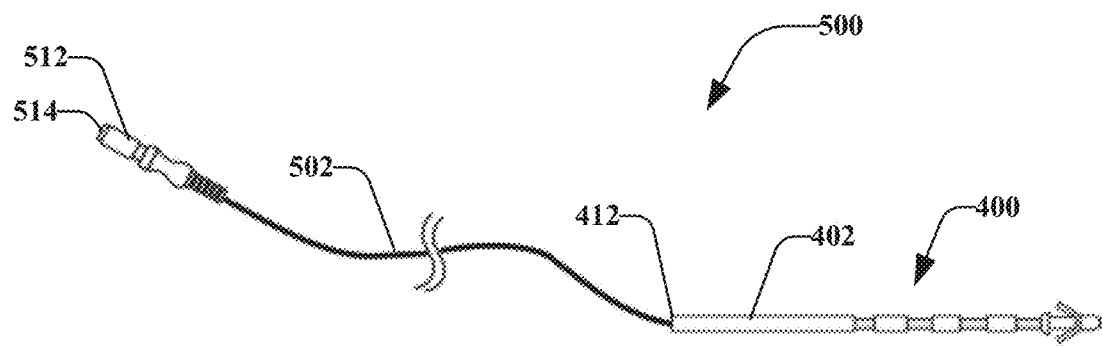
FIG. 5 illustrates an adaptor comprising a percutaneous electrode, in accordance with various disclosed aspects.
Figure 6:
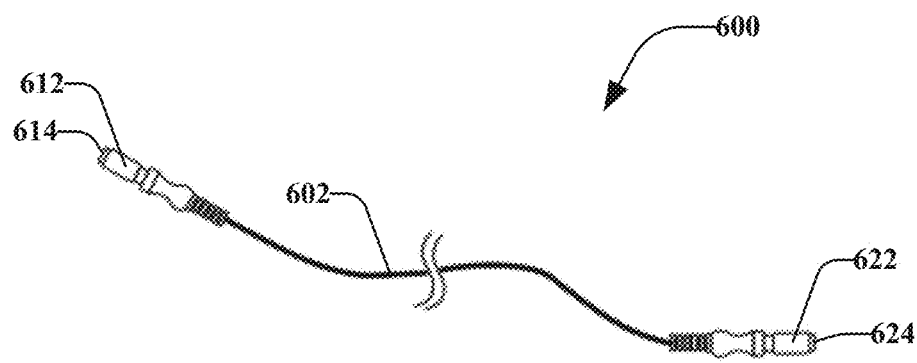
FIG. 6 illustrates an adaptor comprising two connectors, in accordance with various disclosed aspects.
Figure 7:
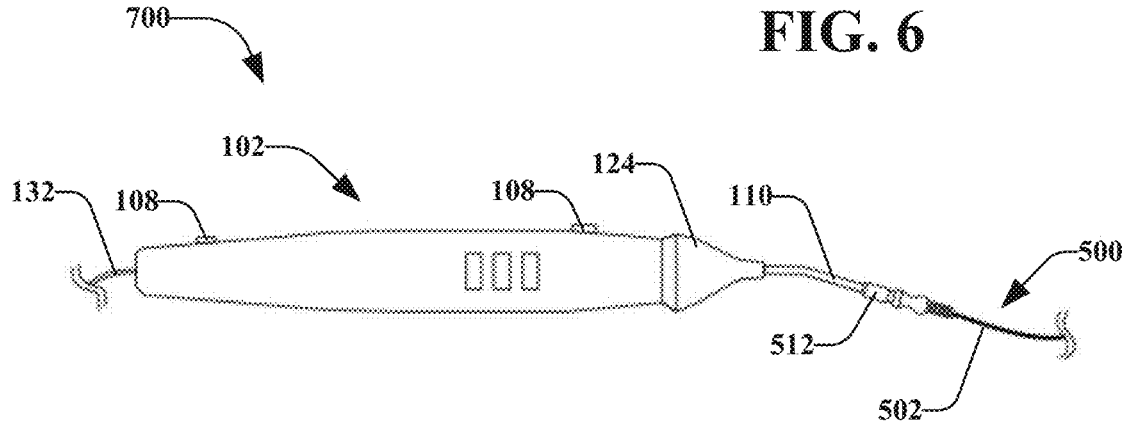
FIG. 7 illustrates the stimulation device of FIG. 1 coupled with an adaptor, in accordance with various disclosed aspects.

Turning now to FIGS. 5-7, with reference to FIGS. 1-4, there are adaptor 500 (which includes percutaneous electrode 400 (and may also include electrode 300 and 450) and a lead wire 502), adaptor 600 (which may be coupled to a stimulation device and/or percutaneous electrode), and stimulation system 700 (which may include stimulation device 102). It is noted that liked named components of the various embodiments may comprise similar aspects, unless context suggests otherwise or a particular distinction is made.

In an embodiment, adaptor 500 may primarily include percutaneous electrode 400, wire 502 and connector 512. Wire 502 may connect terminal end 412 of the percutaneous electrode 400 with connector 512. In an aspect, wire 502 may comprise an insulated wire that is removably or irremovably attached to the percutaneous electrode 400 and/or connector 512. As described herein, the adaptor 500 may be configured to allow a stimulation probe 110 to deliver a stimulation signal below the skin of a subject patient.

In an aspect, connector 512 may include an opening 514 that may receive an operative element. As shown in FIG. 7, the opening 514 may receive the probe 110 of a stimulation device 102. The opening 514 may be tapered to maintain the probe 110 in a friction fit within the connector 512. The connector may further include other retaining features, such as a fastener (e.g., screw, clasp, threaded portions, VEL-CRO, magnet, etc.) to retain the connection between the connector 512 and the probe 110. It is noted that connector 512 may comprise an electrical connection disposed within the connector 512 that may operatively couple an uninsulated or stimulating portion of the probe 110 with the wire 502.

Wire 502 may extend from the connector 512. Wire 502 may be an electrical conductor in electrical connection with probe 110 when probe 110 is operatively inserted into the connector 512. It is noted that the wire 502 may be any appropriate length, such as 24 inches or a length between 12 inches and 48 inches. The lead wire may further be any appropriate gauge, such as 24 AWG wire.

Percutaneous electrode 400 may be coupled to the wire 502 at a terminal end 412. According to an embodiment, the wire 502 may be removably or irremovably coupled to the terminal end. It is noted that the wire 502 may be coupled directly to the terminal end 412 and/or may be coupled indirectly to the terminal end 412, such as through one or more other connectors (not shown). Moreover, wire 502 may be coupled to other portions of the percutaneous electrode 400. In an aspect, the connection between the wire 502 and the percutaneous electrode 400 may be insulated or uninsulated.

As shown in FIG. 6, adaptor 600 may comprise a wire 602 and one or more connectors 612/622. Each connector 612/622 may comprise an opening 614/624. In an aspect, openings 614/624 may comprise similar or different dimensions. For instance, openings 614/624 may be operatively sized and shaped to receive an operative element and/or a percutaneous electrode (e.g., percutaneous electrode 300/400). In at least one embodiment, opening 614 is operatively sized to receive an operative element, and opening 624 is operatively sized to receive a percutaneous electrode. In another aspect, connectors 612/622 may comprise elastomeric materials that may stretch, compress, or otherwise fit different sized components. Moreover, while embodiments disclose connectors 612/622 as female connectors, it is noted that one or more of connectors 612/622 may be a male connector. In another aspect, wire 602 (or 502) may comprise one or more branches or pathways such that connector 614, for example, may be electrically coupled with one or more other connectors through wire 602.

Turning to FIG. 7, and as described herein, system 700 may comprise stimulation device 102 that may be coupled with an adaptor 500 (or other described adaptors). In an aspect, a surgeon may utilize stimulation device 102 during a procedure (e.g., location of a nerve, nerve assessment, etc.) When the procedure is complete, the surgeon may place a percutaneous electrode in a desired location. The surgeon may couple the electrode to the stimulation device 102 via connector 500.

As illustrated, connector 512 may be attached to the probe 110. The surgeon may utilize user interfaces 108 to select a stimulation process. For instance, the surgeon may operatively set the stimulation device 102 to deliver a prolonged stimulation to target tissue. In an aspect, prolonged stimulation may follow completion of a surgical intervention (e.g. nerve repair, nerve release, or nerve transfer). In an aspect, prolonged stimulation may be delivered to a nerve or muscle, distal to site of surgical intervention, to increase muscle viability while the nerve re-grows.

It is noted that the stimulation device 102 may comprise a preprogrammed stimulation process that may operatively generate stimulation signals for prolonged stimulation. In another aspect, user interfaces 108 may allow a user to manually program or adjust stimulation parameters, such as intensity, pattern, time, or the like.

Figure 8:
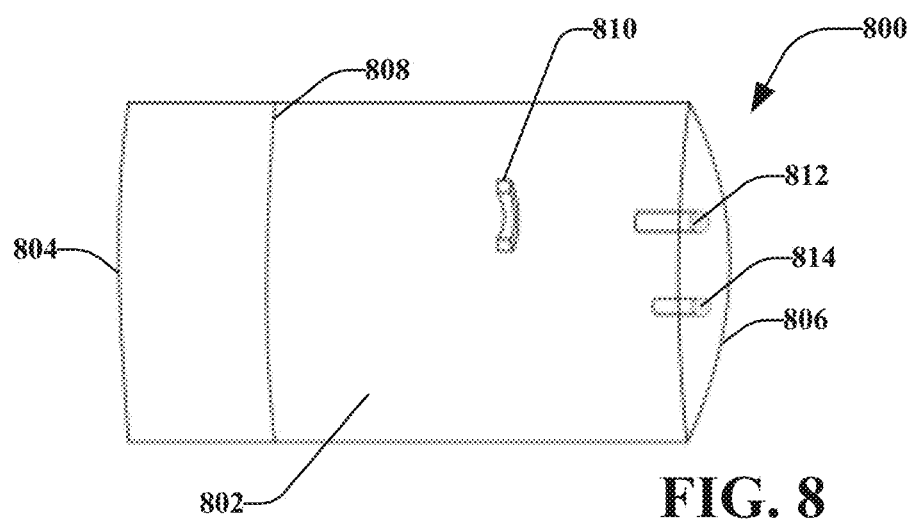
FIG. 8 illustrates a top view of a container for receiving a stimulation device, in accordance with various disclosed aspects.
Figure 9:
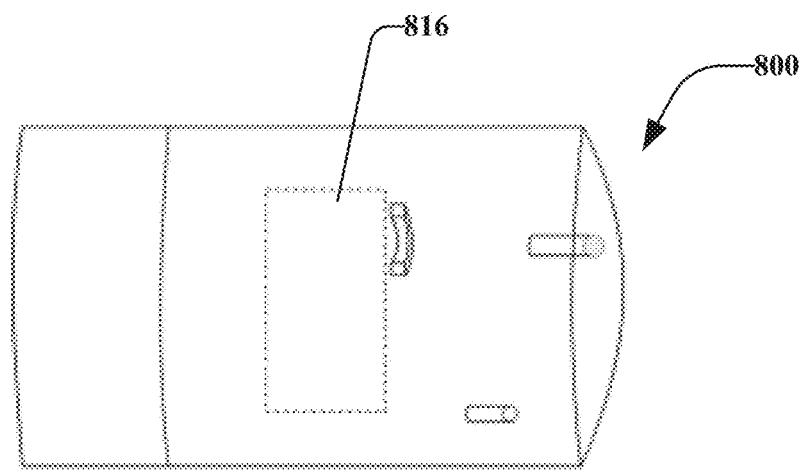
FIG. 9 illustrates a top view of another container for receiving a stipulation device, in accordance with various disclosed aspects.
Figure 10:
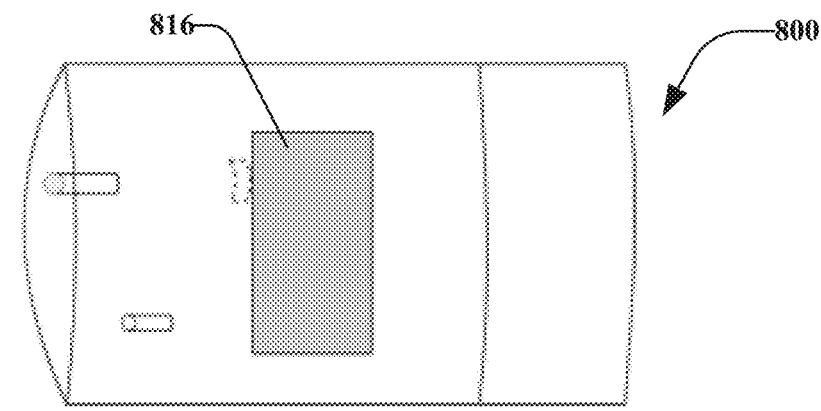
FIG. 10 illustrates a back view of the container of FIG. 9, in accordance with various disclosed aspects.
Figure 11:
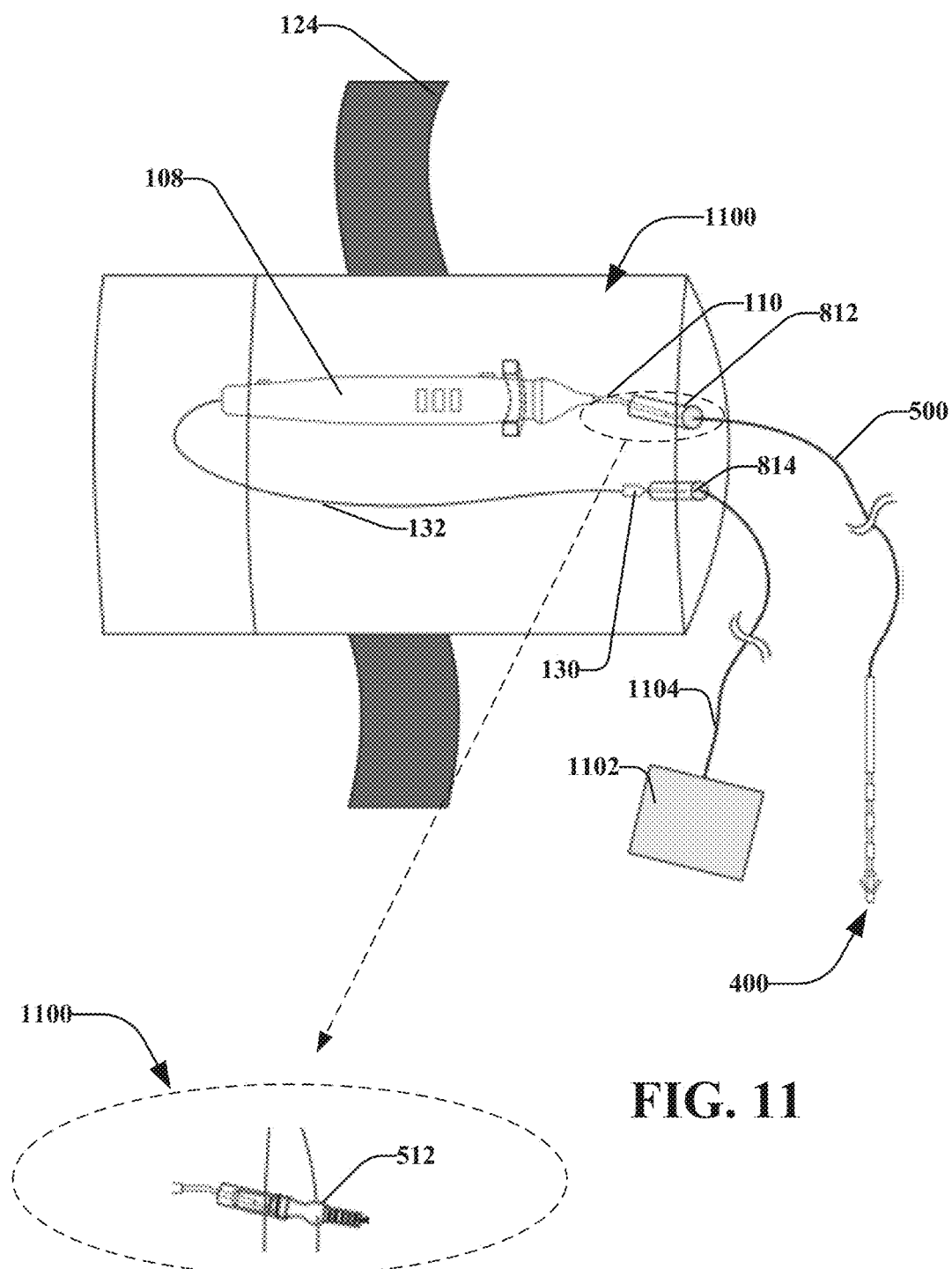
FIG. 11 illustrates a system comprising the container of FIG. 8, the stimulation device of FIG. 1, and electrode connections, in accordance with various disclosed aspects.

FIGS. 8-10 illustrate a container 800 that may operatively receive a stimulation device (e.g., stimulation device 102). FIG. 11 illustrates the stimulation device 102 disposed within the container 800 and coupled with adaptor 500. The container 800 may operatively hold the stimulation device for transitioning a patient to post-op or during post-op. This container may be used to hold a stimulation device that was previously used during the procedure, isolating the device with potential biological contamination (e.g. blood) from the rest of the environment. It is noted that container 800 may comprise various materials, such as one or more of plastic, metal, or the like. In at least one embodiment, container 800 may comprise a sterilized material.

A body 802 of the container 800 may comprise a terminal end 804 and a proximal end 806. The terminal end 804 may comprise an opening 808 that may allow a surgeon to insert the stimulation device 102 in the container 800, and seal the container. It is noted that various other sides or portion of the body 802 may comprise an opening to allow the surgeon to place the stimulation device 102 in the container 800.

According to an embodiment, container 800 may comprise one or more fasteners 810 that may fasten or hold the stimulation device 110 when inserted into the container 800. The fastener 810 may include a hook, clasp, screw, adhesive, or other fastener. For example, fastener 810 may comprise a clasp that may be sized and shaped to allow body 120 of stimulation device 102 to snap into the clasp. In an aspect, the clasp may friction fit with the body 120 to maintain the stimulation device 102 in a general position relative the container 800.

Body 802 may comprise one or more ports, such as port 812 and port 814. Port 812 and port 814 may be disposed and various locations, in an example, port 812 is disposed at a location to allow an operative element of stimulation device 102 to be inserted or otherwise coupled to port 812 when the stimulation device 102 is attached to the fastener 810. Port 814 may operatively receive return electrode 130. It is noted that port 812 and port 814 may be positioned generally proximal each other or may be positioned at other locations.

It is noted that ports 812 and 814 may allow components disposed within the container to be electrically coupled to components disposed outside of the container. In an example, the port 812 may receive a connector (e.g., connector 512 as shown in expanded view 1100). For instance, port 812 may receive a portion of connector 512 and may operatively hold the connector 512 in place (e.g., via a friction fit, fastener, or the like).

In at least one embodiment, the port 812 (and/or 814) may comprise a connector 512 that is built into the container 800. For instance, a user may place the stimulation device 110 in the container 800 and may insert the port 812 into the connector 512 and the return electrode in another connector of port 814. The user may seal the container 800. The user may connect the adaptor 500 to the port 812 from outside of the container 800. In another aspect, the user may connect a return electrode 1102 to the port 814 via a wire 1104 and/or another connector. According to an aspect, this may reduce or prevent the spread of material (e.g., bodily fluids, etc.) on the stimulation device 110 from exiting the container 800 during post-op procedures.

In at least one aspect, body 802 may contain an electrode 816 attached to the outer surface of the container. This electrode 816 may be electrically connected to the return electrode of the stimulation device through port 814. In this embodiment the integrated system would reduce the need for connection of an additional return current electrode such as 1102.

In another aspect shown in FIG. 11, body 802 may include an attachment device, such as a strap 124 that may facilitate attaching the container 800 to an object, such as a patient's limb, a belt, hospital equipment or the like. Various other attachment devices may be utilized, such as hook and loop materials, magnets, elastic, or the like.

Figure 12:
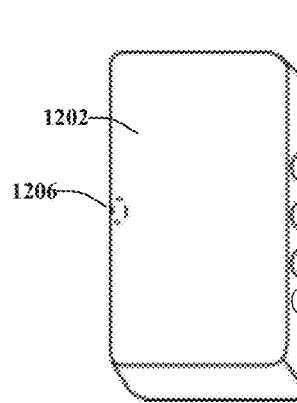
FIG. 12 illustrates a perspective view of a splitter device, in accordance with various disclosed aspects.
Figure 13:
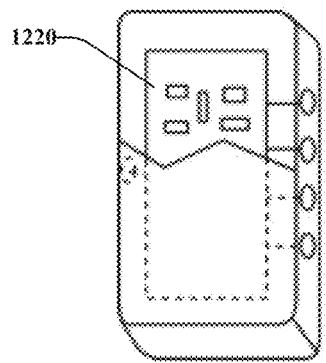
FIG. 13 illustrates a partial cross-sectional, perspective view of a splitter device, in accordance with various disclosed aspects.
Figure 14:
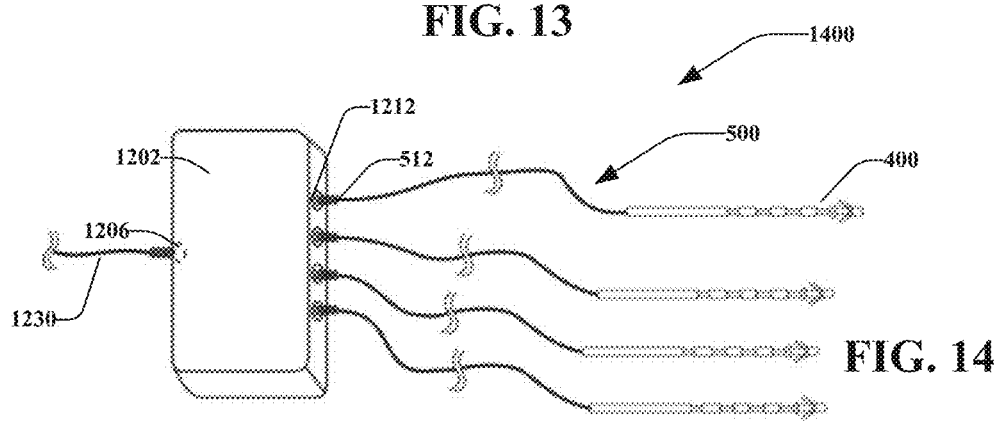
FIG. 14 illustrates a perspective view of the splitter device of FIG. 12 coupled with percutaneous leads, in accordance with various disclosed aspects.

FIGS. 12-14 illustrate a splitter device 1200 that may operatively split a stimulation signal and/or return signal. According to embodiments, the stimulation device 1200 generally include a housing 1202 that houses circuitry 1220. The hosing may include an input port 1206 and one or more output ports 1212, 1214, 1216, and 1218. It is noted that splitter device 1200 may include any number of input or output ports. Internal circuitry therein may be utilized to deliver one input signal to multiple output channels, maintain current level at set output, such as for example at 1.0 or 2.0 mA.

Splitter device 1200 may receive a first wire 1230 via input port 1206. In an aspect, the first wire 1230 may be coupled to a stimulation device (not shown) that may operatively apply a stimulation signal to the input port 1206. The circuitry 1220 may split the stimulation signal to one or more of the output port(s) 1212, 1214, 1216, 1218, which may be coupled to one or more operative elements, percutaneous leads (e.g., percutaneous leads 300, 400, etc.), non-percutaneous leads, or connectors as described herein. In an example, a surgeon may place percutaneous leads 400 in different target tissue in one or more patients. The surgeon may attach the percutaneous leads 400 to the splitter device 1200 and may attach a stimulation device to the splitter device. The stimulation device may apply a prolonged stimulation signal to multiple tissue regions based via the splitter device 1200 and/or percutaneous leads 400.

As described herein, the circuitry 1220 may be an interface between a stimulation signal (received at input port 1206) and divides the input signal to one or more output signals with attached electrodes, selectively output at one or more of output port(s) 1212, 1214, 1216, and 1218. This may allow the stimulation device to utilize additional channels or contacts than otherwise available.

It is noted that the circuitry 1220 may include a power source (e.g., battery) or may receive power from the stimulation device or other external source. In an example, the circuitry may comprise an inductive circuit that operatively stores power in one or more capacitors. According to another embodiment, the input signal received at input port 1206 may supply the power. The circuitry may include the components to ensure output remains within a specified range (e.g. 2.0 mA) whenever a stimulation pulse is delivered to the input port. Moreover, the circuitry 1220 may include a demodulator (e.g. to receive and decode information) and one or more switches or registers that control output to percutaneous leads 400 or other electrical contacts, or the like, In an aspect, the switches may be utilized to detect whether an electrical contact is connected to output port(s) 1212, 1214, 1216, and 1218 such that power may be selectively applied to the ports.

In embodiments the splitter device 1200, or aspects thereof, may be disposed on or within a container (e.g., container 800), or placed on the body outside the container. For instance, the housing 1202 may be disposed within layers of material in the container 800. In another aspect, the circuitry 1220 may be disposed within the material of the container 800 (e.g., the housing may comprise the material of the container). The splitter device 1200 may be sterilized.

According to various embodiments, splitter device 1200 may comprise a clip, fastener, magnet, etc., that operatively attach the splitter device to a patient, clothing, hospital equipment, or the like.

Figure 15:
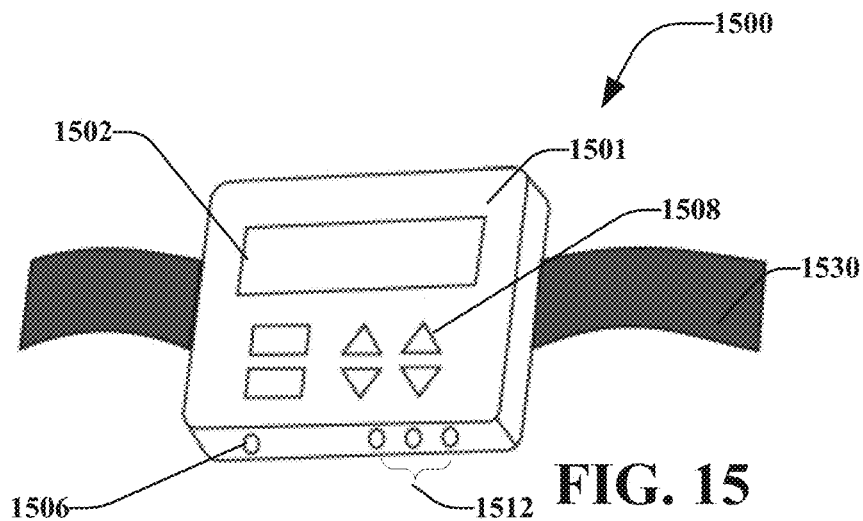
FIG. 15 illustrates a perspective view of another stimulation device, in accordance with various disclosed aspects.
Figure 16:
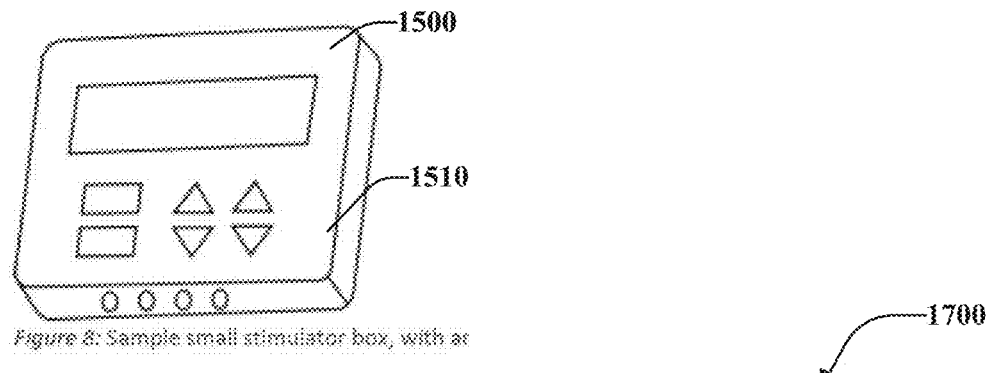
FIG. 16 illustrates an embodiment of the stimulation device in FIG. 15 without a belt, in accordance with various disclosed aspects.
Figure 17:
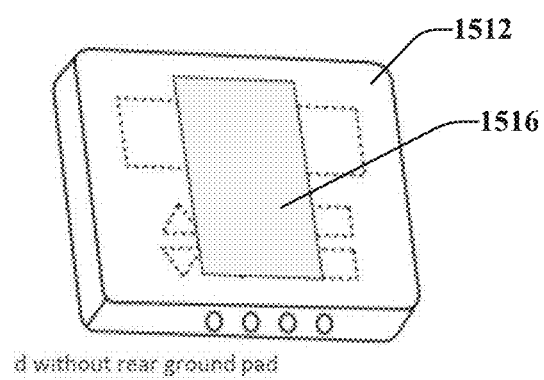
FIG. 17 illustrates a back view of the stimulation device of FIG. 16, in accordance with various disclosed aspects.

FIGS. 15-17 illustrate a stimulation system 1500 primarily comprising a simulation device 1501. The stimulation device 1501 may operatively control stimulation of tissue via one or more stimulating medical devices including, for example, simulation device 1501, probe 1510, percutaneous electrodes 300/400, cutting devices, drilling devices, augers, fixation devices or the like. The stimulation system 1500 may comprise an external stimulator that is selectively attachable ex-vivo a patient. The stimulation system 1500 may comprise a box that may be attached to a patient, such as by adhering to a patch assembly or other adhesive deice attached to a patient, selectively attaching the box to clothing of a patient, including a strap or necklace that a patient can wear to hold the box, using Velcro to attach the box to the patient or patient's clothes, and the like.

In an aspect, the stimulation device 1501 may comprise circuitry that operatively generates an electrical stimulation signal to be applied to a tissue. In an aspect, the stimulation device 1501 may comprise similar functionality as described with reference to other stimulation devices (e.g., stimulation device 102). Moreover, stimulation device 1501 may comprise a user interface 1508, including a display 1502. As described herein, the user interface 1508 may comprise input/output devices that operatively receive user input. A user may interact with the user interface 1508 to adjust parameters of the stimulation signal and/or receive information from the display 1502. For example, the display 1502 may indicate to a user the length of time of the current therapy has left, the time the therapy has been applied, the number of doses of therapy applied and/or number of therapies yet to be applied. By way of a non-limiting example, if the therapy has an intended duration of an hour and twenty minutes of therapy has been applied, the display 1502 may show that there are forty minutes left on the therapy. The display 1502 may comprise an LED screen that can provide any of the information indicated in the present disclosure to the user, patient and/or clinician. Moreover, stimulation device 1501 may comprise a user interface 1508, including a display 1502 and audio feedback. In at least some embodiments, the user interface 1508 may generate an alert that is audible, visual, tactile (e.g., vibration), or combination of the above. For instance, the user interface 1508 may generate alerts to indicate that therapy is complete, a lead has moved, a lead has become disengage, stimulation has been disrupted, an error has occurred, a warning (e.g., power supply is low), or the like. As described herein, the user interface 1508 may comprise input/output devices that operatively receive user input. The display 1502 with or without additional audio tones may display to the user signals recorded on the one or more input ports 1506, which may be connected to other sensors or systems to record physiologic signals such as pressure, electromyograms, stretch, force, or the like. In an aspect, the stimulation device 1501 may include a communication component that may be wired or wireless. For example, the stimulation device 1501 may include a wireless transmitter/receiver configured to communicate via one or more communication protocols (e.g., Wi-Fi, BLUETOOTH, NFC, etc.).

Figure 18:
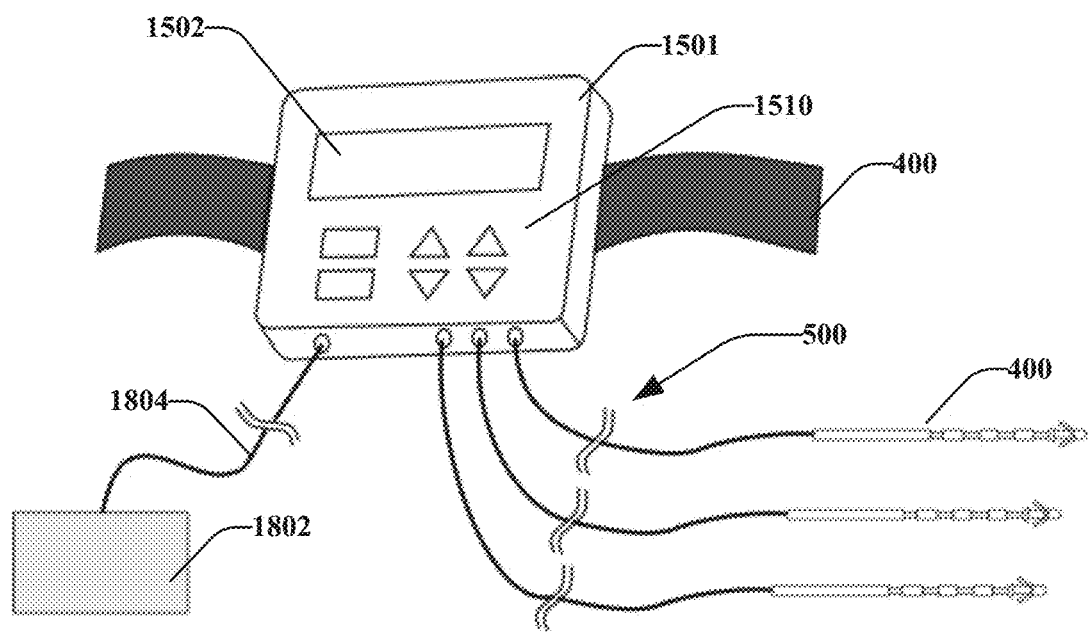
FIG. 18 illustrates an embodiment of the stimulation device in FIG. 15 with one or more percutaneous leads and a return electrode, in accordance with various disclosed aspects.

Stimulation device 1501 may include one or more output ports 1512 that may be operatively coupled with an operative element (e.g., a probe 100), one or more percutaneous leads 400 and/or connectors 500 (e.g., as shown in FIG. 18), or other components. According to one or more embodiments, the stimulation device 1501 may include one or more output ports 1506 that may be coupled to a return electrode 1802 via a wire 1804. It is noted that the return electrode 1802 may comprise a pad-type, needle, or other style electrode as described herein. In an embodiment 1700, the return electrode 1516 may be affixed to the back of the stimulation device 1512.

In embodiments, a first side 1510 of the stimulation device 1501 may comprise user interfaces 1508 as described herein. A second side 1512, which may be generally opposed to the first side 1510, may include return current electrode 1516. The second side 1512 or sides of the device may operatively receive belt 1530. Belt 1530 may be coupled to an object, such as a patient, hospital equipment, or the like. It is noted that stimulation device 1501 may be attachable to objects via other components such as clips, magnets, VELCRO, adhesives, or the like. It is further noted that stimulation device 1501 may be disposed within a container (e.g., container 800), as described with reference to FIGS. 8-11.

As described herein, stimulation devices (e.g., stimulation device 102, 1501, etc.) may operatively apply prolonged stimulation to target tissue. In examples, the prolonged stimulation may be applied post-op (e.g., after completion of a procedure). For instance, a surgeon may create an incision in a patient. The surgeon may utilize a stimulation device to apply a stimulation signal within the incision. Although in some embodiments, no stimulation signal may be utilized during the surgery. Instead, the stimulation may be applied only after the surgery, such as by way of a non-limiting example, during sensory nerve repair, motor or mixed nerve where clinician does not need to or otherwise utilize a stimulator for nerve identification. It is noted that stimulation may be applied to motor or mixed nerves wherein the surgery does not utilize stimulation during the surgery. Regardless of whether stimulation was applied during surgery or after closing of the incision, the surgeon may place a percutaneous lead in or proximal target tissue. The percutaneous lead may be attached to a stimulation device. The stimulation device may apply a prolonged stimulation. In examples, the stimulation device may be the same stimulation device utilized during a procedure or may be a different stimulation device. In another aspect, the stimulation device may be disposed in a container that generally prevents contamination by or movement of the stimulation device.

As described herein, after completion of the stimulation, a surgeon may remove the percutaneous lead. In an aspect, the percutaneous lead may be pulled out of target tissue.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A method for stimulating tissue, comprising:
   placing a lead at or near a target nerve that is proximal to a site of a nerve injury, wherein the lead is operatively attachable to an electrical stimulation device;
   applying an electrical stimulation pulse having a waveform directly to the target nerve through the lead and the electrical stimulation device; and
   directly activating excitable tissue of the target nerve for a therapy duration that comprises one minute or greater but less than 30 minutes in order to alter recovery of the target nerve.

2. The method for stimulating tissue of claim 1, wherein placing the lead comprises placing the lead percutaneously.

3. The method of stimulating the tissue of claim 1, wherein the electrical stimulation device is a handheld electrical stimulation device.

4. The method for stimulating tissue of claim 1, wherein application of the electrical stimulation pulse to the target nerve occurs before surgery.

5. The method for stimulating tissue of claim 1, wherein application of the electrical stimulation pulse to the target nerve occurs during surgery.

6. The method for stimulating tissue of claim 1, wherein application of the electrical stimulation pulse to the target nerve occurs after surgery.

7. The method of claim 1, wherein the electrical stimulation device is disposable.

8. The method of claim 1, wherein the electrical stimulation pulse comprises a biphasic waveform with controlled current during a cathodic phase.

9. The method of claim 1 further comprising dividing an input signal to a plurality of output signals through a corresponding plurality of electrodes extending from the lead.

10. The method of claim 1, wherein the stimulation device utilizes a plurality of channels to deliver the electrical stimulation.

11. The method of claim 1, wherein the stimulation device utilizes a plurality of contacts to deliver the electrical stimulation.

12. The method of claim 1, wherein the electrical stimulation applied has a frequency of between 10 Hz and 100 Hz.

13. The method of claim 1, wherein the electrical stimulation applied has a frequency of between 10 Hz and 40 Hz.

14. The method of claim 1, wherein the electrical stimulation applied has a frequency of 15 Hz to 20 Hz.

15. The method of claim 1, wherein the electrical stimulation applied has an amplitude between 0.1 mA and 20 mA.

16. The method of claim 1, wherein the electrical stimulation applied has an amplitude between 1 mA and 10 mA.

17. The method of claim 1, wherein the electrical stimulation applied has an amplitude between 1 mA and 3 mA.

18. A method for stimulating tissue, comprising:
placing a lead at or near a target nerve that is proximal to a site of a nerve injury, wherein the lead is operatively attachable to an electrical stimulation device;
applying an electrical stimulation having a waveform directly to the target nerve through the lead and the electrical stimulation device; and
directly activating excitable tissue of the target nerve for a therapy duration that comprises one minute or greater but less than or equal to 10 minutes in order to alter recovery of the target nerve.

19. The method of claim 18, wherein the electrical stimulation applied has a frequency of between 10 Hz and 100 Hz.

20. The method of claim 18, wherein the electrical stimulation applied has a frequency of between 10 Hz and 40 Hz.

21. The method of claim 18, wherein the electrical stimulation applied has a frequency of 15 Hz to 20 Hz.

22. The method of claim 18, wherein the electrical stimulation applied has an amplitude between 0.1 mA and 20 mA.

23. The method of claim 18, wherein the electrical stimulation applied has an amplitude between 1 mA and 10 mA.

24. The method of claim 18, wherein the electrical stimulation applied has an amplitude between 1 mA and 3 mA.

25. The method of claim 18, wherein the electrical stimulation comprises a biphasic waveform with controlled current during a cathodic phase.

26. The method of claim 18 further comprising dividing an input signal to a plurality of output signals through a corresponding plurality of electrodes extending from the lead.

27. The method of claim 18, wherein the electrical stimulation device utilizes a plurality of channels to deliver the electrical stimulation.

28. The method of claim 18, wherein the electrical stimulation device utilizes a plurality of contacts to deliver the electrical stimulation.

29. A method for stimulating tissue, comprising:
placing a lead at or near a target nerve, wherein the lead is operatively attachable to an electrical stimulation device;
applying an electrical stimulation directly to the target nerve through the lead and the electrical stimulation device; and
directly activating excitable tissue of the target nerve for a therapy duration that comprises one minute or greater but less than or equal to 10 minutes in order to alter recovery of the target nerve, wherein the electrical stimulation applied has a frequency of between 10 Hz and 40 Hz, an amplitude between 1 mA and 3 mA and a pulse duration of 75 microseconds to 125 microseconds.

30. The method of claim 29, wherein the electrical stimulation device is disposable.

31. The method of claim 29, wherein the electrical stimulation comprises a biphasic waveform with controlled current during a cathodic phase.

32. The method of claim 29 further comprising dividing an input signal to one or more output signals with attached electrodes.

33. The method of claim 29, wherein the stimulation device utilizes a plurality of channels to deliver the electrical stimulation.

34. The method of claim 29, wherein the stimulation device utilizes a plurality of contacts to deliver the electrical stimulation.

* * * * *